US00PP29457P3

(12) United States Plant Patent
Jacobs

(10) Patent No.: US PP29,457 P3
(45) Date of Patent: Jul. 3, 2018

(54) ASTER PLANT NAMED 'ZANASNOWHI'

(50) Latin Name: *Symphyotrichum novi-belgii*
Varietal Denomination: Zanasnowhi

(71) Applicant: Henricus Cornelius Maria Jacobs, Bleiswijk (NL)

(72) Inventor: Henricus Cornelius Maria Jacobs, Bleiswijk (NL)

(73) Assignee: Chrysanthemum Breeders Association Research B.V., Rijsenhout (NL)

( * ) Notice: Subject to any disclaimer, the term of this patent is extended or adjusted under 35 U.S.C. 154(b) by 36 days.

(21) Appl. No.: 14/999,325

(22) Filed: Apr. 25, 2016

(65) Prior Publication Data

US 2017/0311524 P1 Oct. 26, 2017

(51) Int. Cl.
*A01H 5/02* (2018.01)

(52) U.S. Cl.
USPC ..... Plt./355
CPC ..... *A01H 5/025* (2013.01)

(58) Field of Classification Search
USPC ..... Plt./355
CPC ..... A01H 5/025; A01H 5/02; A01H 5/0227
See application file for complete search history.

(56) References Cited

PUBLICATIONS

Royal Van Zanten Royal Collection Pot & Breeding 2015 retrieved on Aug. 16, 2017, retrieved from the Internet at http://www.aaa-flowers.ru/files/uploads/rvz_catalogus_2015_lr_v5.pdf pp. 1-3, 7, 60.*

* cited by examiner

*Primary Examiner* — June Hwu
(74) *Attorney, Agent, or Firm* — C. A. Whealy

(57) ABSTRACT

A new and distinct cultivar of Aster plant named 'Zanasnowhi', characterized by its compact, upright to slightly spreading and mounding plant habit; moderately vigorous growth habit; freely branching growth habit; dense and bushy appearance; freely flowering habit; double-type inflorescences with white-colored ray florets; good postproduction longevity and good container performance.

2 Drawing Sheets

Botanical designation: *Symphyotrichum novi-belgii*.
Cultivar denomination: 'ZANASNOWHI'.

BACKGROUND OF THE INVENTION

The present invention relates to a new and distinct cultivar of Aster plant, botanically known as *Symphyotrichum novi-belgii* and hereinafter referred to by the name 'Zanasnowhi'.

The new Aster plant is a product of a planned breeding program conducted by the Inventor in Rijsenhout, The Netherlands. The objective of the breeding program is to create new compact Aster plants with freely branching habit and attractive double-type inflorescences.

The new Aster originated from a cross-pollination in September, 2012 in Rijsenhout, The Netherlands of a proprietary selection of *Symphyotrichum novi-belgii* identified as code number 181, not patented, as the female, or seed, parent with a proprietary selection of *Symphyotrichum novi-belgii* identified as code number 382, not patented, as the male, or pollen, parent. The new Aster plant was discovered and selected by the Inventor as a single flowering plant within the progeny of the stated cross-pollination in a controlled greenhouse environment in Rijsenhout, The Netherlands in April, 2013.

Asexual reproduction of the new Aster plant by terminal vegetative cuttings was first conducted in Rijsenhout, The Netherlands in May, 2013. Asexual reproduction by cuttings has shown that the unique features of this new Aster plant are stable and reproduced true to type in successive generations.

SUMMARY OF THE INVENTION

Plants of the new Aster have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Zanasnowhi'. These characteristics in combination distinguish 'Zanasnowhi' as a new and distinct Aster plant:

1. Compact, upright to slightly spreading and mounding plant habit.
2. Moderately vigorous growth habit.
3. Freely branching growth habit; dense and bushy appearance.
4. Freely flowering habit.
5. Double-type inflorescences with white-colored ray florets.
6. Good postproduction longevity and good container performance.

Plants of the new Aster differ primarily from plants of the female parent selection in flowering response as plants of the new Aster flower earlier than plants of the female parent selection.

Plants of the new Aster differ primarily from plants of the male parent selection in inflorescence form as plants of the male parent selection have single-type (or daisy) inflorescences.

Plants of the new Aster can be compared to plants of *Symphyotrichum novi-belgii* 'Dasjes', disclosed in U.S. Plant Pat. No. 21,117. In side-by-side comparisons, plants of the new Aster differ from plants of 'Dasjes' in the following characteristics:

1. Plants of the new Aster are more compact than plants of 'Dasjes'.
2. Plants of the new Aster are more freely flowering than plants of 'Dasjes'.

BRIEF DESCRIPTION OF THE PHOTOGRAPHS

The accompanying photographs illustrate the overall appearance of the new Aster plant showing the colors as true as it is reasonably possible to obtain in colored reproductions of this type. Colors in the photographs may differ slightly from the color values cited in the detailed botanical description which accurately describe the colors of the new Aster plant.

The photograph on the first sheet is a side perspective view of a typical flowering plant of 'Zanasnowhi' grown in a container.

The photograph on the second sheet is a close-up view of typical inflorescences of 'Zanasnowhi'.

DETAILED BOTANICAL DESCRIPTION

The aforementioned photographs and following observations and measurements describe plants grown during the autumn in 12-cm containers in a glass-covered greenhouse in Rijsenhout, The Netherlands and under cultural practices typical of commercial Aster production. During the production of the plants, day temperatures ranged from 18.5° C. to 22° C., night temperatures ranged from 18° C. to 21° C. and light levels ranged from 3,500 to 7,000 lux. Plants were pinched one time and were ten weeks old when the photographs and description were taken. In the following description, color references are made to The Royal Horticultural Society Colour Chart, 2001 Edition, except where general terms of ordinary dictionary significance are used.

Botanical classification: *Symphyotrichum novi-belgii* 'Zanasnowhi'.

Parentage:

*Female, or seed, parent.*—Proprietary selection of *Symphyotrichum novi-belgii* identified as code number 181, not patented.

*Male, or pollen, parent.*—Proprietary selection of *Symphyotrichum novi-belgii* identified as code number 382, not patented.

Propagation:

*Type.*—Terminal vegetative cuttings.

*Time to initiate roots, summer.*—About seven days at temperatures about 21° C.

*Time to produce a rooted young plant, summer.*—About nine to ten days at temperatures about 21° C.

*Time to produce a rooted young plant, autumn.*—About eleven to twelve days at temperatures about 21° C.

*Root description.*—Fine, fibrous; close to 155D and 199D in color.

*Rooting habit.*—Freely branching; dense.

Plant description:

*Plant and growth habit.*—Herbaceous double-type potted Aster plant; compact, upright to slightly spreading and mounding plant habit; moderately vigorous growth habit; freely branching growth habit; dense and bushy appearance; about three primary branches each with about one secondary laterals developing per plant, pinching enhances branching potential.

*Plant height.*—About 22 cm.

*Plant width.*—About 25 cm.

*Lateral branches.*—Length: About 9 cm to 12 cm. Diameter: About 1.5 cm. Internode length: About 2 mm to 3.5 mm. Aspect: About 40° from vertical. Strength: Strong. Texture: Smooth, glabrous. Luster: Semi-glossy. Color, developing: Close to 143C. Color, developed: Close to 136C.

Leaf description:

*Arrangement.*—Alternate, simple; sessile.

*Length.*—About 4 cm to 6.5 cm.

*Width.*—About 7 mm to 10 mm.

*Shape.*—Narrowly elliptic.

*Apex.*—Acute.

*Base.*—Attenuate.

*Margin.*—Entire.

*Texture, upper and lower surfaces.*—Smooth, glabrous.

*Luster, upper and lower surfaces.*—Semi-glossy.

*Color.*—Developing leaves, upper surface: Close to 136A. Developing leaves, lower surface: Close to 137A. Fully expanded leaves, upper surface: Close to 136A; venation, close to 147D. Fully expanded leaves, lower surface: Close to 137A; venation, 148D.

Inflorescence description:

*Type and arrangement.*—Double-type (or decorative) inflorescence form with lanceolate-shaped ray florets; inflorescences borne on terminal and axillary branches above and beyond the foliar plane; ray and disc florets arranged acropetally on a capitulum.

*Fragrance.*—None detected.

*Flowering response.*—Under natural conditions, plants flower during the autumn in The Netherlands; plants begin flowering about 5.5 weeks after planting.

*Inflorescence longevity.*—Inflorescences maintain good substance for about four weeks on the plant; inflorescences persistent.

*Quantity of inflorescences.*—Freely flowering habit with about eight to nine inflorescences per lateral branch.

*Inflorescence buds.*—Height: About 8 mm. Diameter: About 6 mm. Shape: Globular. Texture: Smooth, glabrous. Luster: Dull. Color: Close to 150D.

*Inflorescence size.*—Diameter: About 4 cm. Depth (height): About 1.5 cm. Diameter of disc: Inconspicuous.

*Receptacles.*—Height: About 2 mm. Diameter: About 3 mm. Shape: Conical. Color: Close to 139D.

*Ray florets.*—Quantity and arrangement: About 100 to 110 arranged in about six whorls. Length: About 1.5 cm to 2 cm. Width: About 2 mm to 3 mm. Shape: Lanceolate. Apex: Acute. Base: Attenuate. Margin: Entire. Texture, upper and lower surfaces: Smooth, glabrous. Luster, upper and lower surfaces: Moderately glossy. Orientation: Initially upright to semi-upright to eventually close to perpendicular to the peduncle. Color: When opening, upper and lower surfaces: Close to N155D. Fully opened, upper and lower surfaces: Close to N155D; towards the base, close to 144D; color does not change with development.

*Disc florets.*—Quantity and arrangement: If present, about five per inflorescence and randomly arranged at the center of the receptacle; disc florets inconspicuous. Length: About 4 mm. Diameter: About 1.5 mm. Shape: Tubular, elongated; five free apices are acute. Texture, inner and outer surfaces: Smooth, glabrous. Luster, inner and outer surfaces: Slightly glossy. Color, immature, inner and outer surfaces: Close to 154D; color becoming closer to 193D with development.

*Phyllaries*.—Quantity and arrangement: About 45 per inflorescence arranged in about three whorls. Length: About 8 mm. Width: About 1 mm. Shape: Narrowly elliptic. Apex: Acute. Base: Cuneate. Margin: Entire. Texture, upper and lower surfaces: Smooth, glabrous. Luster, upper and lower surfaces: Semi-glossy. Color, upper surface: Close to 137C. Color, lower surface: Close to 137B.

*Peduncles*.—Length, terminal peduncle: About 1 cm to 1.5 cm. Diameter, terminal peduncle: About 1.5 mm. Strength: Strong. Texture: Smooth, glabrous. Luster: Moderately glossy. Color: Close to 138B.

*Reproductive organs*.—Androecium: Present on disc florets only. Quantity of stamens per floret: Five. Filament length: About 0.5 mm. Filament color: Close to 150D. Anther shape: Lanceolate. Anther length: About 0.1 mm. Anther color: Close to 162D. Pollen amount: Scarce. Pollen color: Close to 8C. Gynoecium: Quantity of pistils per floret: One. Pistil length: About 7 mm. Stigma diameter: About 1 mm to 2 mm. Stigma shape: Bifurcate. Stigma color: Close to 1A. Style length: About 5 mm. Style color: Close to 1A. Ovary color: Close to 1A.

*Seeds and fruits*.—Seed and fruit production have not been observed on plants of the new Aster.

Disease & pest resistance: Plants of the new Aster have not been observed to be resistant to pathogens and pests common to Aster plants.

Temperature tolerance: Plants of the new Aster have been observed to tolerate temperatures ranging from about 5° C. to about 32° C. to 33° C.

It is claimed:

1. A new and distinct Aster plant named 'Zanasnowhi' as illustrated and described.

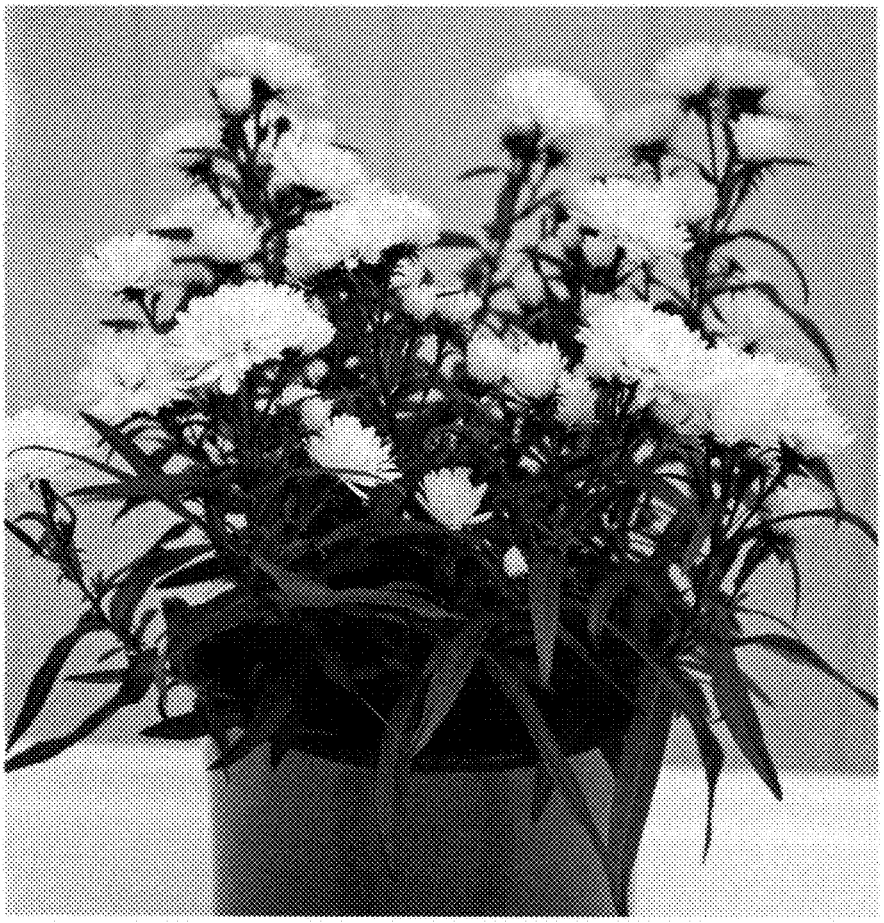

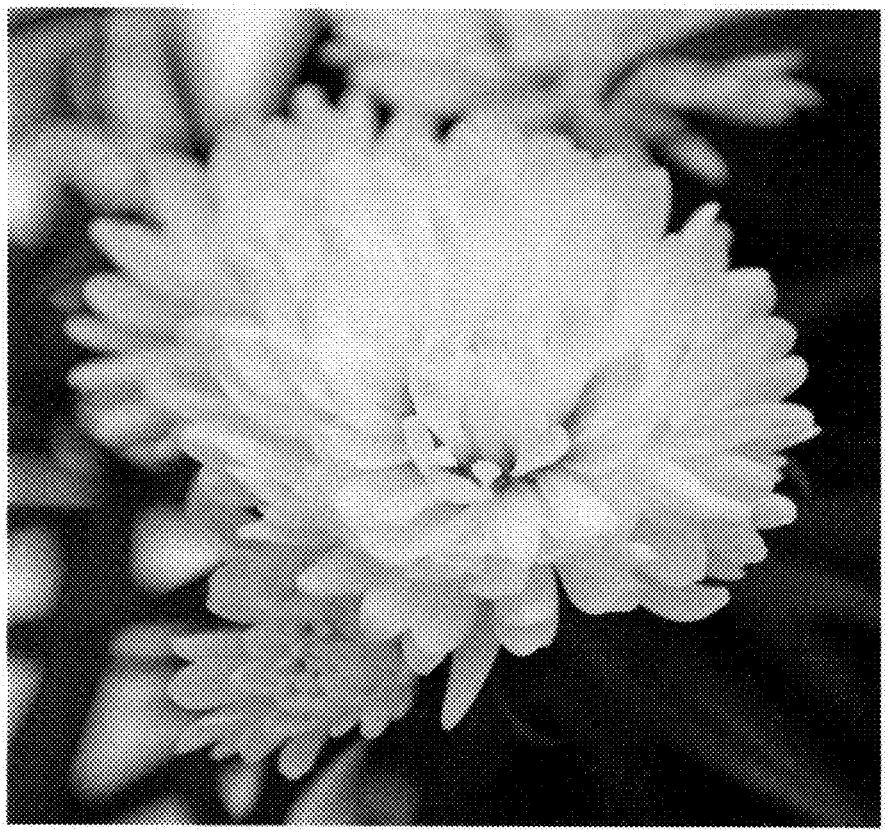

* * * * *